United States Patent [19]

Belanger et al.

[11] Patent Number: 5,556,404

[45] Date of Patent: Sep. 17, 1996

[54] METHOD FOR MAINTAINING FLOW THROUGH CATHETER

[76] Inventors: Alan D. Belanger, 1065 E. Giles Rd., Muskegon, Mich. 49445; Steven M. Schmitt, 2967 McDermott St., Muskegon, Mich. 49444

[21] Appl. No.: 573,652

[22] Filed: Dec. 18, 1995

Related U.S. Application Data

[63] Continuation-in-part of Ser. No. 333,472, Nov. 2, 1994, abandoned.

[51] Int. Cl.⁶ .......................... A61M 39/00; A61M 25/00
[52] U.S. Cl. ........................ 606/151; 606/207; 425/427
[58] Field of Search ............................ 606/151, 153, 606/207; 425/427

[56] References Cited

U.S. PATENT DOCUMENTS

| | | | |
|---|---|---|---|
| 2,965,900 | 12/1960 | Inokouchi | 606/153 |
| 3,258,012 | 6/1966 | Nakayama et al. | 606/153 |
| 3,265,069 | 8/1966 | Healey, Jr. et al. | 606/153 |
| 3,561,448 | 2/1971 | Pefernel | 606/153 |

*Primary Examiner*—Gary Jackson
*Attorney, Agent, or Firm*—Price, Heneveld, Cooper, DeWitt & Litton

[57] ABSTRACT

A dialysis catheter clamp and method according to the invention provide first and second arms pivotally connected. Each arm has a terminal end with a concave clamping surface. The arms pivot about the pivot connection between an open position in which the concave clamping surfaces are space apart and a closed position in which the concave clamping surfaces abut one another and define a closed cylindrical passage between the concave clamping surfaces.

11 Claims, 2 Drawing Sheets

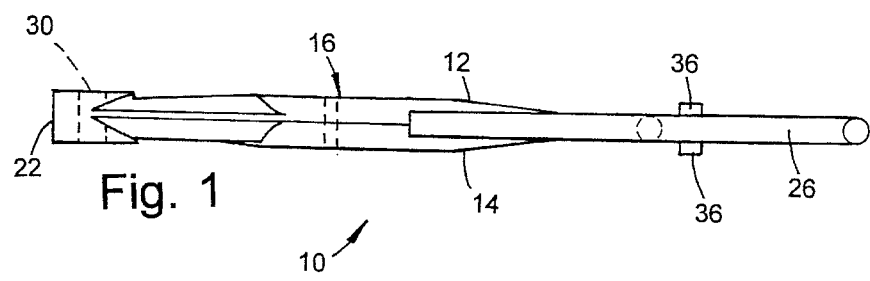
Fig. 1
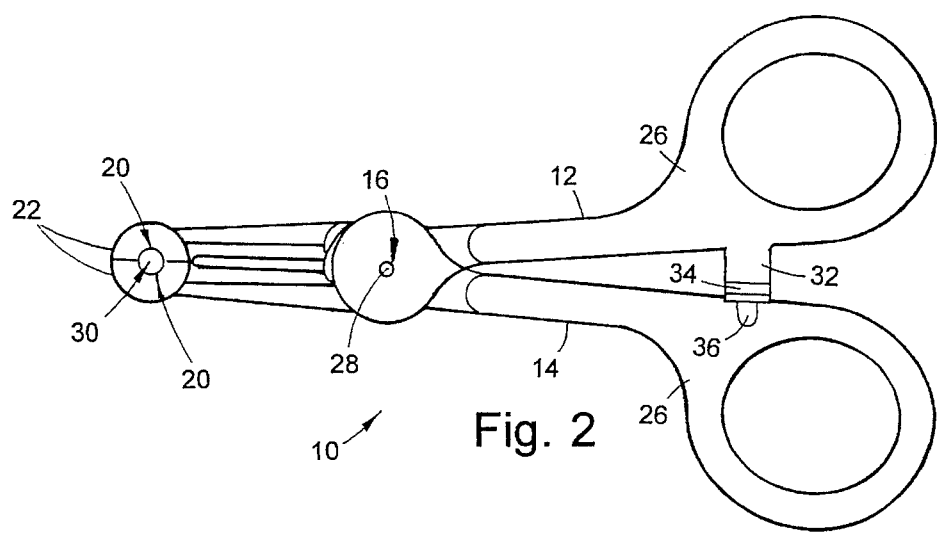
Fig. 2
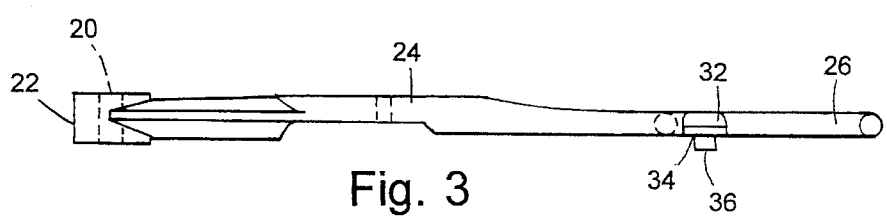
Fig. 3
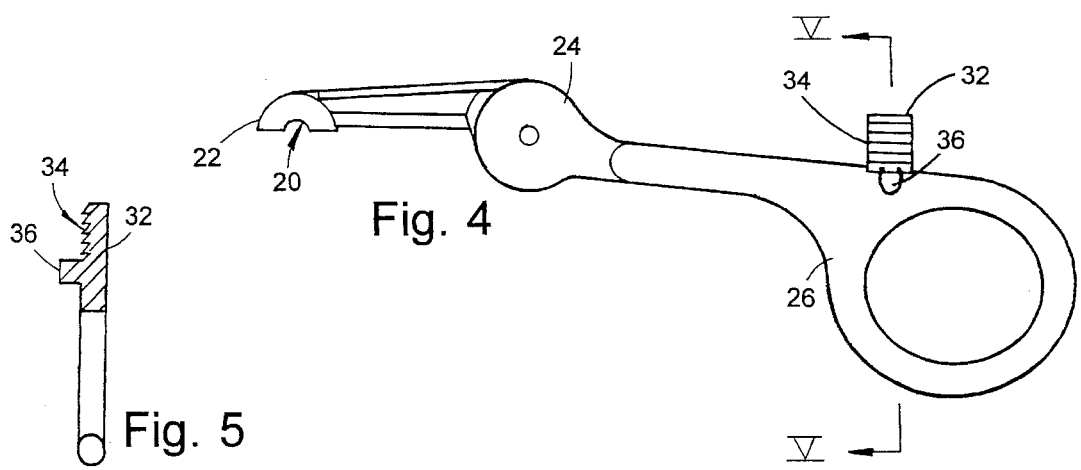
Fig. 4
Fig. 5

METHOD FOR MAINTAINING FLOW THROUGH CATHETER

CROSS REFERENCE TO RELATED APPLICATIONS

This is a continuation-in-part application of Ser. No. 08/333,472 filed Nov. 2, 1994 now abandoned.

BACKGROUND OF THE INVENTION

This invention relates to medical clamping devices and is particularly suitable for clamping a dialysis catheter, or the like.

In the course of various medical procedures, tubular conduits for conducting bodily fluids or medications into or out of a patient's body are used. Because of the relative orientation between a patient and various medical equipment that is utilized in conducting a medical procedure, flexible cubing that extends between the medical equipment and the patient may become kinked and block the flow of fluid. Such kinking often occurs in the vicinity of where the tubing is connected to conduct fluid into or out of the patient.

More particularly in the normal course of blood dialysis, a temporary dialysis catheter is inserted into a patient's blood vessel and extends to a blood dialysis machine. It is a common occurrence for the temporary dialysis catheter to kink in the vicinity of the catheter's entrance into the patient. The catheter kinking significantly reduces, if not entirely blocks, blood flow through the catheter.

The use of a strain relief to eliminate such kinking may be attempted. But, the implementation of a strain relief may typically only relocate the kink to a location adjacent to and unprotected by the strain relief. Also, the use of a strain relief device with delicate equipment may tend to make the equipment bulky with associated use of the equipment becoming awkward.

Thus, one may readily see the need for an effective device to alleviate the occurrence of kinking and fluid blockage in temporary dialysis catheters and the like.

SUMMARY OF THE INVENTION

A clamp and method according to the invention provide non-obtrusive and reliable remedy for assuring proper fluid flow through medical tubing that would otherwise kink and restrict, or entirely block, the flow of medicinal fluids. The invention may be used at any accessible location where a kink occurs along a length of the tubing, rather than being fixed in a particular position at the time of manufacture of the tubing assembly, as is typically the situation with strain relief devices.

A clamp according to the invention includes a first arm with a terminal end; a first arcuate clamping surface at the first arm terminal end; a second arm with a second arm terminal end; a second arcuate clamping surface at the second arm terminal end; and a coupling pivotally connecting the first and second arms to rotate relative to one another about a pivot axis between an open position in which the first and second arcuate surfaces are spaced apart, and a closed position in which the first and second arcuate surfaces abut one another and define a closed cylindrical passage between the arcuate surfaces. In one aspect of the invention, the first and second arms extend from their respective terminal ends and pass the coupling to respective grips, so the clamp may be manipulated by a user in a scissoring action. In another aspect of the invention, the clamp may be provided with a releasable lock to lock the clamp in the closed position and to release the clamp to the open position. Each arm may be provided with cooperating locking portions.

In a further aspect, each arm and its associated arcuate clamping surface, coupling portion, grip, and lock portion may be integrally molded in a one-piece clamping arm assembly. The one-piece clamping arm assembly may be configured so two of the one-piece clamping arm assemblies may be coupled together by inverting one with respect to the other and assembled into a clamp of the invention.

In yet another aspect, the present invention provides a method for maintaining flow through a catheter by use of the instrument and techniques described herein. Catheters, particularly those utilized in administering temporary dialysis, are prone to kinking or otherwise distorting whereby constriction occurs within the catheter tubing. Such constriction obstructs or impedes flow through the catheter and adversely affects dialysis. The device of the present invention when applied to the kink site or point of distortion, forces the wall of the catheter tubing to its original geometry. The instrument can then be locked in such position whereby kinking or constriction is prevented and flow maintained through the catheter.

These and other features, objects, and benefits of the invention will be recognized by those who practice the invention and by those skilled in the art, from the specification, the claims, and the drawing figures.

BRIEF DESCRIPTION OF THE DRAWINGS

FIG. 1 is a top plan view of a temporary dialysis catheter clamp according to the invention;

FIG. 2 is a side elevational view of the clamp of FIG. 1;

FIG. 3 is the view of FIG. 1 with one of the two clamping arm assemblies removed;

FIG. 4 is the view of FIG. 2 with one of the two clamping arm assemblies removed; and FIG. 5 is a sectional view along section line V—V of FIG. 4.

DESCRIPTION OF THE PREFERRED EMBODIMENTS

Figure 6:
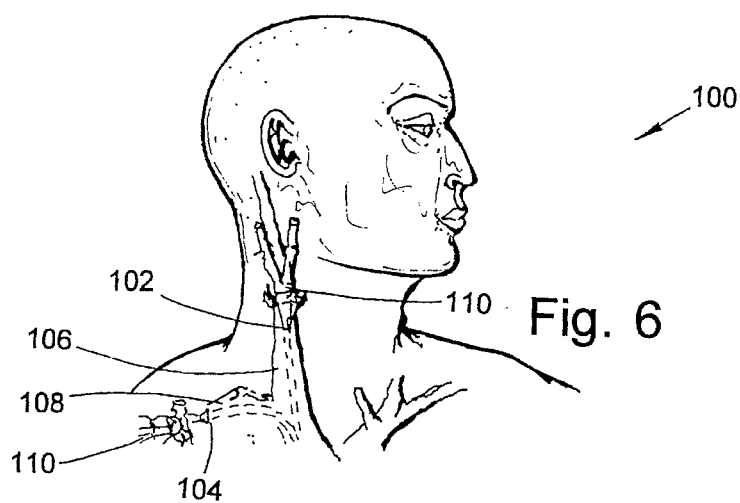
FIG. 6 is an illustration of a human patient and two possible sites for placement of a catheter.

A preferred embodiment of a temporary dialysis catheter clamp according to the invention is generally shown in the drawing FIGS. 1–6 and identified by reference number 10 (FIGS. 1 and 2). The clamp 10 most preferably has two identical, one-piece clamping arm assemblies 12 and 14 which are coupled at a pivot coupling 16 to provide a scissor action clamp.

As is shown in greater detail in FIGS. 3 and 4, each one piece clamping arm assembly 12 or 14 may be formed with an arcuate, concave clamping surface 20 at a terminal end 22. The arm 12 or 14 extends from the terminal end 22 to a coupling or pivot portion 24 and farther to a grip 26 at an end of the arm opposite the terminal end 22 where the clamping surface 20 is located. Each one-piece clamping arm assembly 12 or 14 may be constructed of any suitable structural or engineering material that is appropriate and approved for non-invasive medical Instruments, including stainless steel and nylon resin plastics, for example. More specifically, Zytel® 8018 NC010 nylon resin plastic, available from the Du Pont Company, may be successfully employed in fabricating a clamp 10 according to the invention.

The two clamping arm assemblies 12 and 14 are pivotally connected together by a pivot pin 28 (FIG. 2). Pivot pin 28 may take any suitable form as is well known for configuring a member to interconnect two halves of a plier-like or scissor-like tool, including a rivet, a through bolt, or a generally T-shaped projection extending from one clamping arm assembly to interconnect with a cooperating slot in the opposing clamping arm assembly, for example.

To lock clamp 10 in a closed position, in which the clamping surfaces 20 abut one another and define a closed cylindrical passage 30 (FIG. 2), each of the clamping arm assemblies 12 and 14 is provided with a latch member 32 (FIGS. 2–5), as is known to lock a hemostat or the like. Each latch member 32 is preferably integrally formed in one piece with the respective clamping arm assembly 12 and 14 and is provided with a series of saw-tooth steps 34 (FIGS. 4 and 5) for cooperating engagement with the opposing latch member 32. Each latch member 32 is also provided with a latch stop 36 that extends generally perpendicular to the series of teeth 34, at the base of the latch member, and provides a positive stop to locate the opposing latch member 32, and in turn the two clamping arm assemblies 12 and 14, in the fully closed and locked position.

Each of the clamping surfaces 20 is sized and configured to define a closed cylindrical passage 30 that corresponds to the outside size and shape of a selected medical tubing. Thus, various clamps 10 may be provided to cover a range of tubing sizes and cross-sectional shapes. Although, a non-circular cross-sectional shape would be unusual.

In use to remedy a kinked tubing situation, clamp 10 is opened to space the clamping surfaces 20. The kinked portion of tubing is seated in one of the two opposing clamping surfaces 20. And, clamp 10 is manipulated from the open to the closed position. In closing clamp 10, the two clamping surfaces 20 approach one another and abut to define the closed cylindrical passage 30. In so doing, the kinked portion of tubing becomes seated in the other of the two clamping surfaces 20 and the two clamping surfaces 20 squeeze the kinked tubing and forces the external wall of the tubing back to its designed circular shape, conforming to the closed cylindrical passage 30. Thus, the fluid passage defined through the tubing is restored and a restricted or blocked fluid flow is alleviated.

In a particularly preferred embodiment, clamp 10 is utilized to prevent kinking or other distortion in a catheter such as a temporary dialysis catheter 110 illustrated in FIG. 6, and thereby ensure that flow is maintained though the catheter. FIG. 6 illustrates a patient 100 in need of dialysis and two typical sites 102 and 104 for dialysis catheter 110. Location 102 is formed by an incision along the external jugular vein depicted in FIG. 6 as 106. The second location 104, is formed by an incision along the subclavian vein depicted in FIG. 6 as 108. Other sites for insertion and placement of dialysis catheter 110 include the femoral in the groin region.

Figure 7:
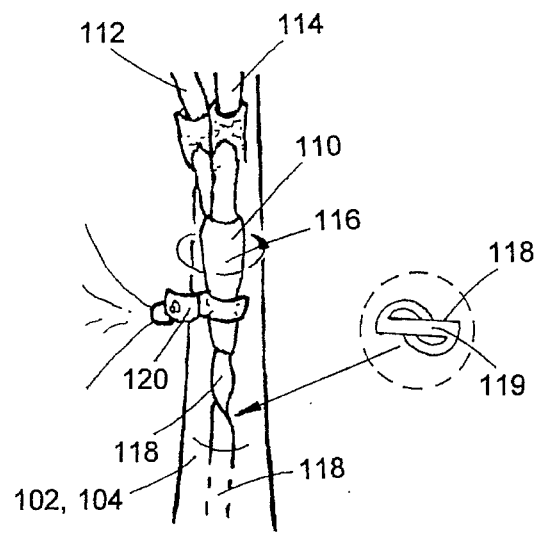
FIG. 7, an illustration of a temporary dialysis catheter inserted within a vein, depicts a kinked catheter tubing.

FIG. 7 illustrates catheter 110 inserted into a vein of a patient at location 102 or 104. As is known by those skilled in the art, catheter 110 generally comprises two ports for transferring blood to and from the vein in which catheter 110 is inserted. Inlet port 112 is a tubular portion of catheter 110 extending between a dialysis unit (not shown) and patient, through which treated blood is transferred to the patient. Outlet port 114, similar to port 112, extends between the previously noted dialysis unit and patient and transfers blood from the patient to the dialysis unit for subsequent treatment. Catheter 110 further comprises a manifold 116 which connects ports 112 and 114 to a channelled tube portion, designated as 118 in FIG. 7. Manifold 116 directs blood from ports 112 an 114 to respective halves of divided tube 118. Tube 118 comprises an interior wall 119 extending throughout its length, or a majority thereof, from manifold 116 to the distal end of 118 (not shown). Wall 119 functions to divide one interior region of tube 118 through which blood flows from port 112, from the other interior region of tube 118 through which blood flows to port 114.

Once catheter 110 is properly inserted into a vein of a patient, divided tube 118 extends approximately 3 to 5 inches within the vein. Catheter 110 is secured to the patient by suturing catheter 110 at suture wings 120 to the patient. Once secured to a patient, catheter 110 remains with the patient generally from about 2 to about 4 weeks. For individuals receiving dialysis treatments, connection to the catheter may occur up to 3 or 4 times a week.

A common problem associated with dialysis is difficultly in maintaining a dialysis blood flow above a threshold level over the course of the dialysis treatment session. During such sessions, which generally range from about 2 to about 5 hours, it is generally necessary to maintain a dialysis blood flow of at least 200 ml per minute. If dialysis flow rates drop below that or some other threshold level, treatment becomes subtherapeutic. Despite careful attention give during dialysis sessions, it is common for flow rates to drop below the threshold and for treatment to become subtherapeutic.

The present inventors have discovered that the underlying cause for reductions in dialysis flow rates is constrictions or kinks in the divided wall portion 118 of the dialysis catheter. Kinking can result from numerous factors including improper insertion and suturing to the patient, excessive manipulation of catheter 110 and/or tube 118 during dialysis, and movement by the patient during dialysis. When the portion 118 of catheter 110 is twisted, as illustrated in FIG. 7, the exterior walls of tube 118 tend to collapse against interior wall 119 thereby causing flow constriction. Kinking or other constriction generally occurs along the exposed length of divided tube 118 between manifold 116 at suture wings 120 and the incision in the vein, where contact and friction between the outer periphery of tube 118 and the vein generally occurs.

Figure 8:
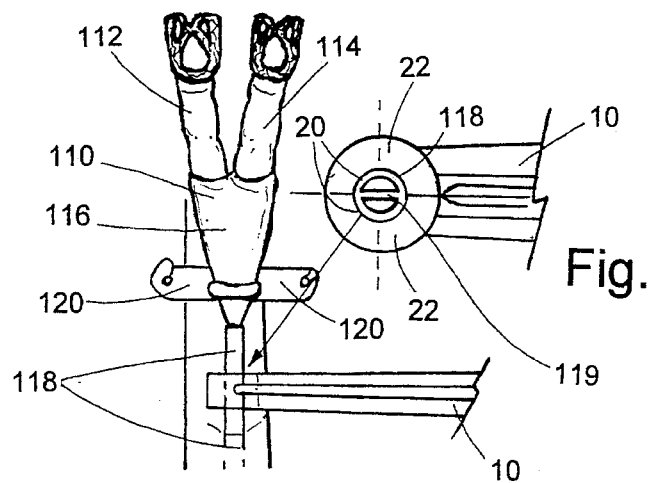
FIG. 8 is an illustration of the preferred embodiment device of the present invention being used to prevent a kink in a catheter tube and thereby maintain flow through the catheter.

Prevention of constriction along divided tube portion 118, and thus maintenance of flow in catheter 110, is performed according to the present invention by applying clamp 10 to the region of tube 118 at which constriction or kinking is occurring as illustrated in FIG. 8. That is, the outer periphery of tube 118 is placed between clamping surfaces 20 of clamp 10 and the clamp manipulated to a closed position so that tube portion 118 is contacted and seated between terminal ends 22 of clamp 10. Clamp 10 is locked in place whereby the proper configuration and geometry of tube 118 is maintained. Once locked, clamp 10 can be left in such position over the entire dialysis treatment period.

Testing was performed to determine the effectiveness of the device and the techniques of the present invention. A dialysis catheter, similar to previously described catheter 110, was inserted into a saline source and connected to a dialysis unit. Dialysis was initiated and steady state flow rate measured. Constrictions were then introduced at the divided tube portion of the catheter and the decrease in flow rate measured. Constrictions were formed by rotating or twisting the catheter along the divided tube portion. Upon formation of a constriction or kink and measurement of reduced flow rate, the instrument of the present invention was then applied at the point of constriction as described herein and the increase in flow rate measured. The results of this testing are set forth below. Improvements in flow rate are based upon the increase in flow rate occurring at the respective degree of constriction.

| Extent of Constriction or Kink | Percent Improvement Utilizing Present Invention |
| --- | --- |
| 50 degrees | 33% |
| 60 degrees | 48% |
| 70 degrees | 60% |
| 80 degrees | 70% |

It is remarkable that such high percentages of improvement in flow rates can be achieved upon kinked tubing. Furthermore, it is unexpected and surprising that the extent of improvement dramatically increases as the extent of kinking increases.

It will be understood by those who practice the invention and by those skilled in the art, that various modifications and improvements may be made to the invention without departing from the spirit of the disclosed concept. The scope of protection afforded is to be determined by the claims and by the breadth of interpretation allowed by law.

The embodiments of the invention in which an exclusive property or privilege is claimed are defined as follows.

1. A method of remedying the situation of having a kinked tubing, comprising the steps of:

providing a first concave clamping surface;

seating the tubing kink in the first concave clamping surface;

providing a second concave clamping surface;

also seating the tubing kink in the second concave clamping surface; and squeezing said first and said second concave clamping surfaces together to define a cylindrical passage between said first and said second clamping surfaces and press the tubing kink into conformity with the cylindrical passage defined between said first and said second concave clamping surfaces.

2. The method defined in claim 1 further including the step of providing a first clamping arm extending from said first clamping surface and providing a second clamping arm extending from said second clamping surface.

3. The method defined in claim 2 further including the step of pivotally interconnecting said first and second clamping arms to rotate said first and second clamping surfaces about an axis of rotation between an open position in which said first and second clamping surfaces are spaced apart, and a closed position in which said first and second clamping surfaces abut one another and define said closed cylindrical passage between said first and second clamping surfaces.

4. The method defined in claim 3 further including the step of providing a releasable lock to lock said first and second clamping surfaces in said first position and release said first and second clamping surfaces to said open position.

5. A method of promoting flow of blood through a dialysis catheter having a channelled tube disposed within a vein of a patient, said method comprising:

identifying a kink site or point of constriction in said channelled tube;

providing a clamping device comprising a first concave clamping surface and a second concave clamping surface;

seating a constricted portion of said channelled tube between said first and second concave clamping surfaces; and compressing said first and second concave clamping surfaces together to define a cylindrical passage between said first and second clamping surfaces and thereby causing said channelled tube to conform to said cylindrical configuration between said first and second concave clamping surfaces, whereby flow of said blood through said catheter is promoted.

6. The method of claim 5 wherein said channelled tube comprises a divider wall extending along the interior diameter of said tube, said divider wall also extending across at least a majority of the length of said channelled tube.

7. The method of claim 5 wherein said flow of blood is maintained above a therapeutic flow rate by seating and compressing said portion of said channelled tube between said first and second concave clamping surfaces of said clamping device.

8. The method of claim 7 wherein said therapeutic flow rate is 200 ml per minute.

9. A method of removing a flow constriction in a catheter tube, said method comprising:

providing a clamping device comprising first and second concave clamping surfaces;

seating said constricted tube between said first and second concave clamping surfaces; and positioning said first and second concave clamping surfaces together to define a cylindrical passage between said first and second clamping surfaces and thereby causing said tube portion to conform to said cylindrical configuration between said first and second concave clamping surfaces, whereby said constriction is removed.

10. The method of claim 9 wherein said catheter tube comprises an interior wall dividing the interior of said tube into two distinct portions along at least a majority of the length of said catheter tube.

11. The method of claim 10 wherein said constriction in said catheter tube occurs as a result of twisting of said catheter tube.

\* \* \* \* \*